United States Patent
Müller et al.

(10) Patent No.: US 10,987,136 B2
(45) Date of Patent: Apr. 27, 2021

(54) SYSTEM COMPRISING A MEDICAL APPARATUS AND A MEDICAL DEVICE, MEDICAL APPARATUS AND SURGICAL METHOD

(71) Applicant: SpineWelding AG, Schlieren (CH)

(72) Inventors: Andrea Müller, Winterthur (CH); Domenico Romeo, Wohlen (CH); Philipp Bernhard, Thun (CH); Mario Weiss, Diessbach bei Büren (CH)

(73) Assignee: SPINEWELDING AG, Schlieren (CH)

( * ) Notice: Subject to any disclaimer, the term of this patent is extended or adjusted under 35 U.S.C. 154(b) by 0 days.

(21) Appl. No.: 16/923,291

(22) Filed: Jul. 8, 2020

(65) Prior Publication Data
US 2020/0337731 A1     Oct. 29, 2020

Related U.S. Application Data (62) Division of application No. 15/754,885, filed as application No. PCT/CH2016/000126 on Sep. 27, 2016, now Pat. No. 10,722,270.

(30) Foreign Application Priority Data

Sep. 30, 2015    (CH) .................................... 01423/15

(51) Int. Cl.
    *A61F 2/46*            (2006.01)
    *A61B 17/68*          (2006.01)
                      (Continued)

(52) U.S. Cl.
    CPC ........ *A61B 17/686* (2013.01); *A61B 17/0491* (2013.01); *A61B 17/68* (2013.01);
                      (Continued)

(58) Field of Classification Search
CPC combination set(s) only.
See application file for complete search history.

(56) References Cited

U.S. PATENT DOCUMENTS

| 6,921,264 B2 | 7/2005 | Mayer et al. |
| 7,335,205 B2 | 2/2008 | Keschlimann et al. |
| (Continued) | | |

FOREIGN PATENT DOCUMENTS

| WO | 2008/034277 | 3/2008 |
| WO | 2009/010234 | 1/2009 |
| (Continued) | | |

OTHER PUBLICATIONS

International Preliminary Report on Patentability dated Apr. 3, 2018 (Apr. 3, 2018), Application No. PCT/CH2016/000126, 8 pages.

*Primary Examiner* — Sameh R Boles
(74) *Attorney, Agent, or Firm* — Rankin, Hill & Clark LLP (57) ABSTRACT

A system for establishing an anchorage in an operation site of a human or animal patient with the aid of a material having thermoplastic properties and vibration energy. The system includes a transmitting piece connected or connectable to an energy source for generating vibration energy, and a housing with an opening. The transmitting piece is arranged moveably within the housing, the opening being adapted to the transmitting piece for a distal portion of the transmitting piece to be able to protrude from the opening. The system also includes a driver being activatable for exerting a compression force on the transmitting piece, and a thermoplastic element arranged to be compressible between the transmitting piece and a counter element by the compression force. Furthermore, the system is equipped for shock-free initial positioning and pre-pressing of the transmitting piece against the thermoplastic element.

15 Claims, 7 Drawing Sheets

(51) Int. Cl.
*A61B 17/86* (2006.01)
*A61B 17/88* (2006.01)
*A61B 17/04* (2006.01)
*A61B 17/00* (2006.01)

(52) U.S. Cl.
CPC .......... *A61B 17/864* (2013.01); *A61B 17/866* (2013.01); *A61B 17/8872* (2013.01); *A61B 17/8685* (2013.01); *A61B 2017/00955* (2013.01); *A61B 2017/8655* (2013.01)

(56) References Cited

U.S. PATENT DOCUMENTS 8,623,050 B2 * 1/2014 Lehmann ........... A61B 17/0401
606/232
2011/0046670 A1 2/2011 Lehmann et al.

FOREIGN PATENT DOCUMENTS

| WO | 2009/010247 | 1/2009 |
| WO | 2009/055952 | 5/2009 |
| WO | 2009/132472 | 11/2009 |
| WO | 2010/045751 | 4/2010 |
| WO | 2010/096942 | 9/2010 |
| WO | 2010/127462 | 11/2010 |
| WO | 2011/054123 | 5/2011 |
| WO | 2012/041376 | 4/2012 |

* cited by examiner state of the art

Fig. 1a state of the art

Fig. 1b state of the art

Fig. 2a state of the art

SYSTEM COMPRISING A MEDICAL APPARATUS AND A MEDICAL DEVICE, MEDICAL APPARATUS AND SURGICAL METHOD

CROSS REFERENCE TO RELATED APPLICATION

This application is a divisional application of U.S. application Ser. No. 15/754,885 filed Feb. 23, 2018, which itself is a National Stage Application of PCT/CH2016/000126 filed Sep. 27, 2016 and claims priority to Swiss Application CH 01423/15 filed Sep. 30, 2015, all of which are expressly incorporated herein by reference.

BACKGROUND OF THE INVENTION

Field of the Invention

The invention is in the field of medical technology, and relates to a system including a medical apparatus and a medical device, and it further relates to the medical apparatus and to a surgical method in which the system is applicable. The system and the method according to the invention serve in particular for establishing an anchorage in hard tissue or corresponding replacement material or for augmenting hard tissue in an operation site in a human or animal patient with the aid of a material having thermoplastic properties and vibration energy. The material having thermoplastic properties is initially solid, is then liquefied in situ, and, in a liquefied state, is displaced to contact or penetrate the hard tissue or replacement material, by e.g. penetrating the trabecular network of bone tissue, to form, together with the hard tissue or replacement material, a sort of composite material. The system includes a plurality of elements in an assembled configuration and has two parts: the apparatus, which is removed from the operation site on completion of the surgical method and the device which remains within the body of the patient. Depending on embodiment and application some system elements may belong to either one of the apparatus and the device, i.e. may remain in the body or may be removed.

Description of Related Art

The publication WO2011/054123 discloses a system including a medical apparatus and a medical device, and a surgical method which serve the same purpose as stated above for system and method according to the invention. The named publication discloses a device to be anchored in hard tissue which device includes a sleeve with an axial opening and radial fenestration (in short: fenestrated sleeve), and it further includes a pin which includes the material having thermoplastic properties (in short: thermoplastic pin), wherein sleeve and pin are adapted to each other for the pin to be able to be introduced into the axial opening of the sleeve from a proximal sleeve side and to be kept therein by a correspondingly closed or partly closed distal sleeve side. The apparatus to be used for anchoring the device in the hard tissue includes a combination of an energy source and a transmitting piece, the combination being arranged in a housing allowing limited axial movement of the combination within the housing and allowing protrusion of a distal portion of the transmitting piece out of the housing. The apparatus further includes a driver that biases the combination of transmitting piece and energy source against the distal opening of the housing. The transmitting piece and the fenestrated sleeve are adapted to each other such that a distal portion of the transmitting piece is introducible into the sleeve to contact the proximal end of the pin when the latter is positioned in the sleeve.

The energy source of the disclosed apparatus is a generator of vibration energy, in particular ultrasonic vibration energy, including e.g. piezoelectric elements, and it is activated by an alternating voltage supplied to the energy source via a cable leading into the housing. The transmitting piece is a sonotrode coupled directly or via a booster to the energy source. The combination of the source of ultrasonic vibration energy and the transmitting piece is acoustically de-coupled from the housing.

The driver of the disclosed system is a driver spring arranged between the transmitting piece (e.g. via the energy source) and the housing and exerting an axial force on the transmitting piece, which force (compression force) is used for compressing the pin, for displacing the liquefied pin material through the fenestration of the sleeve and into the hard tissue and for advancing the transmitting piece for compensation of the shortening of the pin due to the displacement of the liquefied pin material. Before the liquefaction process, the transmitting piece is locked in an initial position and the driver spring is kept in a pre-loaded configuration.

The system of device and apparatus as disclosed in the above named publication is used in the following manner: The pin is introduced into the sleeve, wherein the sleeve may be positioned in an opening in bone tissue. The transmitting piece is in its initial position and the driver spring in its pre-loaded configuration. The housing is fixed to the sleeve or fixedly positioned relative to the sleeve, such that the transmitting piece is able to enter the sleeve and to contact the pin. The energy source is activated and the driver spring is activated (released from its pre-loaded configuration). Activation of the driver spring causes the transmitting piece to be driven against the pin and therewith the pin to be compressed between the transmitting piece and the sleeve, while activation of the energy source causes energy to be transmitted via the transmitting piece to the pin. If the energy is vibration energy this means that the pin is vibrated within the sleeve, causing friction between pin and sleeve and therewith heating and liquefaction of the pin material. The compression force exercised by the driver spring presses the liquefied material out of the fenestration of the sleeve, where it e.g. penetrates the trabecular network of the walls of the opening in the bone tissue in which the sleeve is positioned. After de-activation of the energy source, the displaced pin material re-solidifies and e.g. constitutes together with the trabecular network a sort of composite and a positive fit connection between the sleeve and the bone tissue.

A similar system of apparatus and device is described in the publication WO 2009/010234.

Methods for establishing an anchoring in hard tissue or corresponding replacement material or for augmenting hard tissue with the aid of in situ liquefaction of a material having thermoplastic properties and energy, in particular ultrasonic vibration energy, which methods form the basis of the method according to the invention are disclosed e.g. in the following publications: U.S. Pat. Nos. 7,335,205, 6,921,264, WO2008/034277, WO2009/010247, WO2009/055952, WO2009/132472, WO2010/045751, WO2010/127462.

In addition to the above briefly described systems as disclosed in the publications WO2011/054123 and WO 2009/010234 in which the material having thermoplastic properties is provided by a pin that is positionable in a fenestrated sleeve and that is compressed between the sleeve and the transmitting piece, the publications WO2008/034277, WO2009/055952, and WO2010/127462 further disclose systems in which the material having thermoplastic properties is provided by a tube surrounding a distal portion of the transmitting piece, which tube is compressed between the distal end of the transmitting piece and a counter element.

Figure 1A:
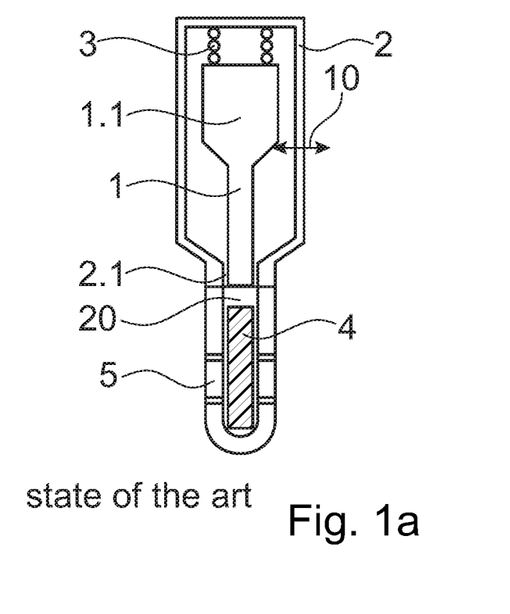
FIGS. 1a and 1B illustrate, in a very schematic manner, a system according to the state of the art including a thermoplastic pin and a fenestrated sleeve and constituting a basis for system and method according to the invention (FIG. 1a: the assembled system before the liquefaction process.

Two exemplary embodiments of the system according to the state of the art are illustrated in FIGS. 1a/b and 2a/b.

The full disclosure of all publications cited above is incorporated herein by reference.

SUMMARY OF THE INVENTION

It is the object of the present invention to improve the above briefly described known medical system of apparatus and device, and the above briefly described surgical method, which serve for establishing an anchorage in hard tissue or corresponding replacement material or for augmenting hard tissue with the aid of in situ liquefaction of a material having thermoplastic properties and vibration energy, in particular ultrasonic vibration energy, which is applied to the material having thermoplastic properties.

Experience with the systems and methods according to the above briefly described state of the art shows, that difficulties occurring on liquefaction of the material having thermoplastic properties can be reduced or eliminated and that the quality of the resulting anchorage or augmentation can be improved when measures are taken for preventing shock-like compression of the element including the material having thermoplastic properties (in short: thermoplastic element). One cause for the effect may be that preventing shock-like compression of the thermoplastic element, in particular when in the form of a pin or tube of a small diameter, may prevent deformation, e.g. buckling, of the pin or tube, which may have a negative effect on the liquefaction process.

According to the invention, prevention of shock-like compression of the material having thermoplastic properties is achieved by carrying out a preparatory step preceding the liquefaction process. In this preparatory step, the transmitting piece is positioned and pre-pressed in a controlled manner, in particular shock-free, against the thermoplastic element. During the preparatory step, the transmission piece is driven by a positioning force, which is relevantly smaller than the compression force, to close a possible gap that may exist in the assembled system between the thermoplastic element and system elements between which the thermoplastic element is to be compressed, and the thermoplastic element is pre-compressed. Only then, the full compression force is applied, either following the preparatory step automatically or activated by a person handling the system.

The method according to the invention includes the following steps:
  assembling the system elements, wherein the transmitting piece is in its initial position and the thermoplastic element (pin or tube) is arranged between the transmitting piece and a counter element (sleeve or collar);
  positioning the system relative to hard tissue or corresponding replacement material;
  positioning and pre-pressing the transmitting piece against the thermoplastic element by applying a positioning force smaller than a compression force (step of system preparation);
  compressing the thermoplastic element between the transmitting piece and the counter element by applying the compression force, activating the energy source, and keeping the compression force applied and activation of the energy source going for a time sufficient for liquefaction of at least part of the material having thermoplastic properties to be liquefied and to be displaced for contacting or penetrating the hard tissue or the hard tissue replacement material (step of liquefaction).

Figure 13:
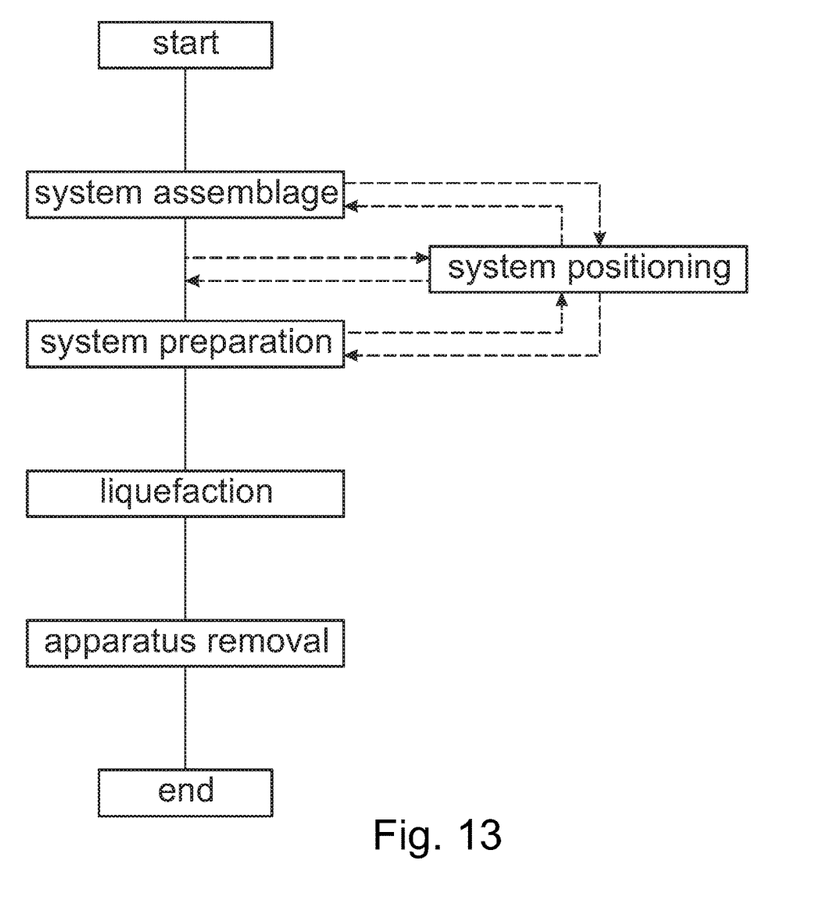
FIG. 13 is a general flow-diagram of the method according to the invention.

The step of positioning the system relative to the hard tissue is to be completed before both compression force and energy source are active. According to the application of the system and in particular according to the device to be anchored in the tissue, the step of positioning the system is carried out in its entirety (positioning of system) or in part steps (e.g. part step of positioning apparatus and part step of positioning device) during system assemblage, after system assemblage or after system preparation (step of positioning and pre-stressing transmitting piece). It is possible also, to even position the system relative to the tissue, when the driver is already fully activated, i.e. the thermoplastic element is fully compressed, but the energy source is not yet activated. A general step sequence of the method according to the invention is illustrated in FIG. 13.

In a preferred embodiment, the fenestrated sleeve is a cannulated screw that is screwed into the hard tissue as part of the step of positioning the system relative to the hard tissue. As further parts of the step of positioning the system, the pin is then introduced into the positioned screw and the housing is fixed to the proximal end of the screw. Only then, the preparatory step of positioning and pre-stressing the transmitting piece against the pin is carried out. The source of vibration energy is preferably activated simultaneously with the application of the compression force, but may be activated alternatively before the preparatory step or when the compression force is already acting.

As used already in the above short description of systems according to the state of the art and as valid also in the following description of system and method according to the invention, the transmitting piece has a proximal end connected or connectable to the energy source and a distal end to be positioned against the thermoplastic element. When the system elements are arranged relative to each other all have a distal and a proximal end corresponding to their arrangement relative to the transmitting piece and they all have a longitudinal axis extending between the proximal end and the distal end, wherein the longitudinal axes of the elements arranged in the system are oriented substantially in parallel to each other or are coinciding.

As mentioned further above for the systems according to the state of the art and as also valid for the system according to the invention, the thermoplastic element is a pin or a tube. As counter element, the system with the pin includes a fenestrated sleeve being pressed against the distal pin end for compressing the pin; the system with the tube includes a proximal collar, being pressed against the proximal tube end for compressing the tube.

The system according to the invention is constituted by the apparatus and the device, wherein the device constitutes the anchorage or augmentation, i.e. is left in the hard tissue, while the apparatus is removed. The sleeve of the pin/sleeve system can be left or removed and therefore depending on the application may be part of the device or the apparatus. The transmitting piece of the tube/collar system may be removed (belonging to the apparatus) or at least a distal part of this transmitting piece may be left in the tissue (belonging to the device). The same applies to the collar, which may be an integral part of the housing (belonging to the apparatus) or, as e.g. integral part of the tube, may be left in the tissue (belonging to the device).

The housing, the transmitting piece (possibly fixedly coupled to the energy source), the thermoplastic element (pin or tube) and the counter element (sleeve or collar), when arranged in the system, form together with the driver a load frame. According to the invention, this load frame is substantially closed (and slightly pre-loaded) in the preparatory step of positioning and pre-pressing and it is finally loaded in the step of compressing.

The same as with the apparatus and systems according to the state of the art, it is valid also for the system and the method according to the invention that the material having thermoplastic properties is, e.g., a thermoplastic polymer, copolymer or polymer mixture based, e.g., on polylactide. The thermoplastic polymer may contain a filler for reinforcement of the polymer or for other purposes. The material having thermoplastic properties is chosen in view of the anchorage or augmentation to be established with its help, in particular in view of the load the anchorage or the augmentation is to bear, and it is chosen in view of the energy to be used for its liquefaction.

The system according to the invention may include a driver spring for driving the transmitting element. However, other types of drives are applicable also, such as, e.g., a hydraulic, pneumatic or electric drive.

The preparatory step of positioning and pre-pressing the transmitting piece against the thermoplastic element and the following step of compressing the thermoplastic element may be carried out in the following ways:
- for the step of positioning and pre-pressing: activate the driver and restrict the driver force acting on the thermoplastic element with the aid of a braking element; for the step of compressing: de-activate the force restriction;
- for the step of positioning and pre-pressing: apply the driver force of an auxiliary drive to the transmitting piece; for the step of compressing: activate the driver.
- for the step of positioning and pre-pressing: activate the driver and control the driver for an initially slow driver force increase; for the step of compressing: no further activation needed.

BRIEF DESCRIPTION OF THE DRAWINGS

The invention is described in further detail in connection with the appended Figs., wherein:

FIG. 1b: the assembled system during the liquefaction process);

FIG. 1b: the assembled system during the liquefaction process);

DESCRIPTION OF THE PREFERRED EMBODIMENTS

All the systems illustrated in the following figures include an energy source to which the transmitting piece is fixed, wherein the combination of energy source and transmitting piece is arranged within the housing. Such an arrangement is in particular suitable in a case in which the apparatus is a hand-held apparatus and the energy source is a generator of ultrasonic vibration energy. However, all the features described in connection with the following figures are also applicable for systems in which the energy source is situated outside of the housing and connected to the transmitting piece with a possibly flexible connector passing through a wall of the housing.

All the systems illustrated in the following figures include a driver spring for driving the transmitting piece and compressing the thermoplastic element. However, as already mentioned further above, the system according to the invention may also include alternative drivers, wherein the elements for restricting the driver force or for applying an auxiliary force may need to be adapted accordingly.

In all figures, same reference numerals designate same elements or elements serving the same function.

Figure 1B:
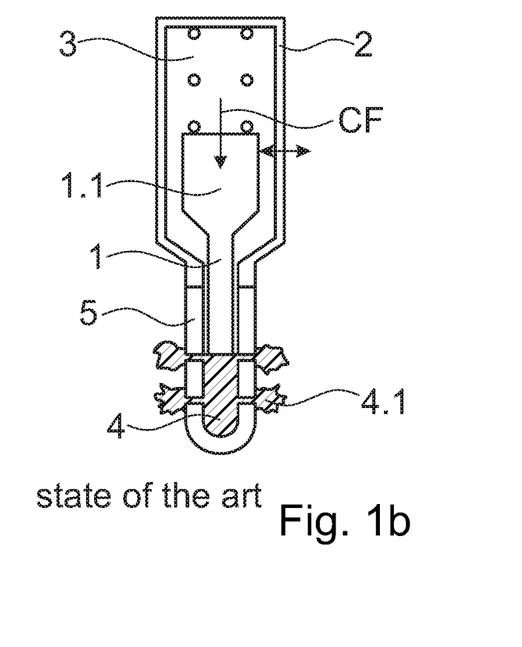

FIGS. 1a and 1b illustrate a system and a method according to the state of the art, system and method serving for establishing an anchoring in hard tissue or corresponding replacement material or for augmenting hard tissue in an operation site in a human or animal patient with the aid of a material including thermoplastic properties which is liquefied in situ by applying energy, in particular vibration energy (e.g. ultrasonic vibration energy). The system is shown in FIG. 1a in an assembled state, ready for the liquefaction process and in FIG. 1b during the liquefaction process.

The system is very schematically illustrated, wherein for further detail reference is made to the initially cited publications, in particular to the publication WO2011/054123. The system includes a transmitting piece 1 fixed to an energy source 1.1, a housing 2 and a driver spring 3, which elements constitute the medical apparatus and are removed from the operation site after the anchoring or augmenting process. The system further includes a pin 4 including the material having thermoplastic properties (thermoplastic element) and a fenestrated sleeve 5 (counter element), wherein at least the pin 4 constitutes the device that is left in the operating site after the anchoring or augmenting process, whereas the sleeve 5 may belong to the device (left in the operation site) or to the apparatus (removed from the operation site).

In the assembled system, as illustrated in FIG. 1*a*, the transmitting piece 1 is arranged in the housing 2 allowing limited axial movement of the transmitting piece 1 relative to the housing 2 such that the transmitting piece 1 protrudes more or less from the distal opening 2.1 of the housing. The driver spring 3, which in the shown embodiment is a compression spring, is arranged to act between the proximal end of the housing 2 and the transmitting piece 1 (in the illustrated embodiment via the energy source 1.1) and it is designed for biasing the transmitting piece 1 towards the distal end of the housing 2. In the assembled system, which is ready for the liquefaction process, the driver spring 3 is preloaded and the transmitting piece 1 kept in an initial position (e.g. most proximal position) by a releasable lock 10 that can be activated for locking the transmitting piece 1 in the initial position and the driver spring 3 in a preloaded configuration, and de-activated for releasing the transmitting piece 1 and activating the driver spring 3. The lock 10 is illustrated very schematically as a double arrow and, in the configuration as shown in FIG. 1*a*, is in its locking position (left position).

For the liquefaction process, which is shown in FIG. 1*b*, the pin 4 is compressed between the transmitting piece 1 and the inside of the sleeve 5 by activation of the compression spring 3, i.e. by bringing the lock 10 into its releasing position (right position) and energy is applied to the pin 4 through the transmitting piece 1, wherein the compression force CF exercised by the driver spring 3 keeps the pin in a compressed state and dislocates the liquefied pin material through the fenestration of the sleeve 5 onto the outer surface of the sleeve 5 (displaced pin material 4.1). During the liquefaction process the pin 4 gets shorter and the distal end of the transmission piece 1 is moved deeper into the sleeve by the compression force CF.

Depending on the initial position of the transmitting piece 1 and the axial length of the pin 4 and the depth of the opening of the sleeve 5, there may exist a gap 20 between the distal face of the transmitting piece 1 and the proximal face of the pin 4 or, depending on the orientation of the system and the fit of the pin 4 in the sleeve 5, between the distal end of the opening in the sleeve 5 and the distal face of the pin 4. For being able to compress the pin 4 and to transmit energy into the pin 4, this gap 20 needs to be closed, which according to the state of the art is effected on release of the driver spring 3 immediately following its activation, resulting in a shock-like compression of the pin. Of course it is possible to adapt the system elements and their relative arrangement such, that in the assembled system, which is ready for the liquefaction process, there is no gap 20. However, if the same apparatus is to be used e.g. with pins 4 of differing lengths and/or sleeves 5 with openings of differing depths this will not be so in most cases.

Further embodiments of the system as shown in FIGS. 1*a* and 1*b* may include instead of the driver spring 3 (compression spring) a tension spring arranged between the transmitting piece 1 (or the energy source 1.1) and the distal end of the housing 2, which tension spring, when activated, pulls the transmitting piece 1 towards the distal end of the housing.

Figure 2A:
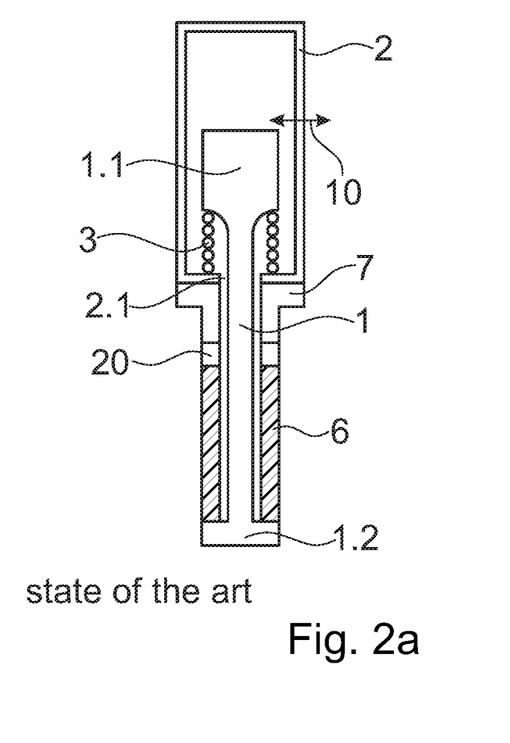
FIGS. 2a and 2b illustrate, in a very schematic manner, a system according to the state of the art including a thermoplastic tube and a collar and constituting a basis for system and method according to the invention (FIG. 1a: the assembled system before the liquefaction process.
Figure 2B:
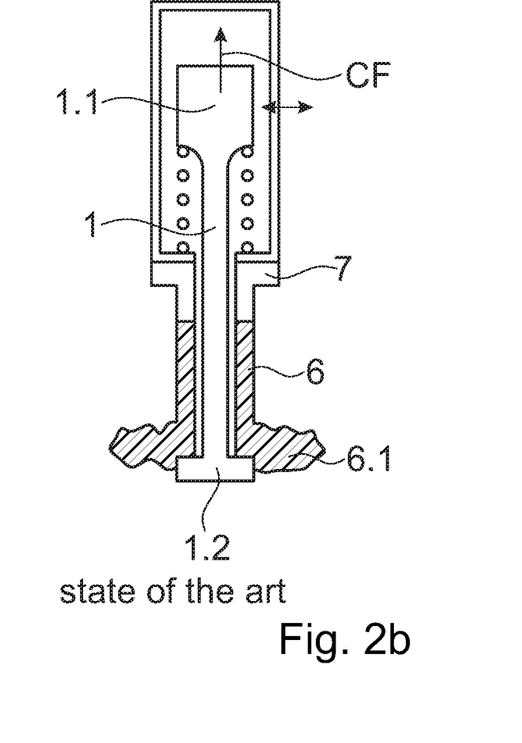

FIGS. 2*a* and 2*b* illustrate a system and a method according to the state of the art, the system and the method serving the same purpose as the system and method illustrated in FIGS. 1*a* and 1*b*. The system is shown in FIG. 2*a* in an assembled state, ready for the liquefaction process, and in FIG. 2*b* during the liquefaction process.

The system is very schematically illustrated, wherein for further detail reference is made to the initially cited publications, in particular to the publications WO2008/034277, WO2009/055952, and WO2010/127462. The system includes a transmitting piece 1, possibly fixed to an energy source 1.1, a housing 2 and a driver spring 3, constituting the apparatus to be removed from the operating site after the anchoring or augmenting process. The system further includes a tube 6 including the material having thermoplastic properties (thermoplastic element) and a collar 7 (counter element), wherein at least the tube 6 constitutes the device, which is left in the operating site, whereas the collar 7 and possibly also a distal portion 1.2 of the transmitting piece 1 may belong to the device (left in the operating site) or to the apparatus (removed from the operating site).

In the assembled system as illustrated in FIG. 2*a*, the transmitting piece 1 and the energy source 1.1 are arranged in the housing 2, wherein this arrangement allows limited axial movement of the transmitting piece 1 relative to the housing 2 for the distal end of the transmitting piece 1 to protrude more or less from the distal opening 2.1 of the housing. The driver spring 3 is a compression spring arranged to act between the distal end of the housing and the transmitting piece 1 (in the illustrated embodiment via the energy source 1.1), wherein the driver spring 3 is designed for biasing the transmitting piece 1 towards the proximal end of the housing 2. The distal portion 1.2 of the transmitting piece 1 extends through the collar 7 and the tube 6, wherein the collar 7 is positioned between the distal opening 2.1 of the housing 2 and the proximal end of the tube 6. The collar 7 may be a separate element, it may be fixed to or be an integral part of the housing 2, or it may be an integral part of the tube 7.

In the assembled system, which is ready for the liquefaction process the driver spring 3 is preloaded e.g. by locking the transmission piece 1 in an initial position (e.g. most distal position), with the aid of the releasable lock 10. The lock 10 is illustrated very schematically as double arrow and, in the configuration as shown in FIG. 2*a*, in its locking position (left position).

For the liquefaction process, which is shown in FIG. 2*b*, the tube 6 is compressed between the distal end of the transmitting piece 1 and the collar 7 by activation of the driver spring 3, i.e. by bringing the lock 10 into its releasing position (right position). Furthermore, energy is applied to the tube 6 through the transmitting piece 1, wherein the compression force CF exercised by the driver spring 3 keeps the tube 6 in a compressed state and dislocates the liquefied tube material radially away from the tube 6 (displaced tube material 6.1). During the liquefaction process the tube 6 gets shorter and the distal end of the transmitting piece 1 is moved further towards the housing 2 by the compression force CF.

Depending on the initial position of the transmitting piece 1 and the axial lengths of the transmitting piece 1 and the tube 6, there may, in the assembled system, exist a gap 20 between the proximal face of the tube 6 and the distal face of the collar 7 or between the proximal face of the counter element 7 and the housing 2, or, depending on the orientation of the system and the fit of the tube 4 on the transmitting piece 1, between the distal end of the tube 6 and the distal end of the transmitting piece 1. For being able to compress the tube 6 and to transmit energy into the tube, this gap 20 needs to be closed, which according to the state of the art is effected by the compression force exercised by the driver spring 3 immediately after its activation, resulting in a shock-like compression of the tube 6. As stated above for the system illustrated in FIGS. 1a and 1b, it is of course possible to adapt the system elements such, that no gap 20 occurs when the system is assembled. However, if the same apparatus is to be used e.g. with tubes 6 of different lengths this will not be so in most cases.

Further embodiments of the system as shown in FIGS. 2a and 2b include instead of the driver spring 3 (compression spring) a tension spring arranged between the transmitting piece 1 (or the energy source 1.1) and the proximal end of the housing 2, which tension spring, when activated, biases the transmitting piece 1 towards the proximal end of the housing.

All the systems illustrated in the following FIGS. 3 to 12 illustrate the system and method according to the invention based on the state of the art system according to FIGS. 1a and 1b, i.e. on a systems including a pin (thermoplastic element) and a fenestrated sleeve (counter element) and a driver in a form of a compression spring. However, all the features described in connection with the FIGS. 3 to 12 are also applicable for systems based on the state of the art system illustrated in FIGS. 2a and 2b, wherein the features described in the following need to be adapted for the compression force and the smaller positioning force to be oriented in the opposite direction, i.e. from the distal side of the system to its proximal side.

Figure 3:
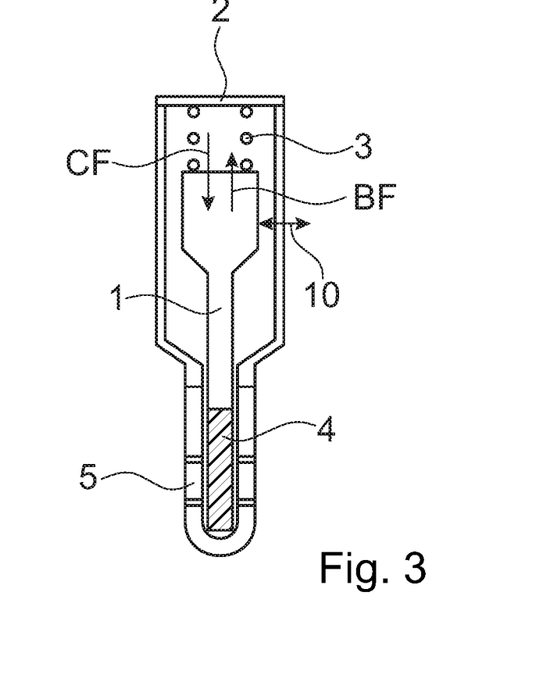
FIG. 3 illustrates, in a very schematic manner, an exemplary embodiment of system and method according to the invention, wherein the compression force is initially restricted.

FIG. 3 illustrates an exemplary embodiment of the system and the method according to the invention, the system being shown in a configuration ready for the liquefaction step, i.e. the system elements are assembled and the preparatory step is carried out, i.e. the transmitting piece 1 is positioned and pre-pressed against the pin 4. In this embodiment shock-like compression of the pin 4 is achieved by activating the driver spring 3 (releasing lock 10) and simultaneously restricting the force exerted by the driver spring 3 to the pin 4. Such restriction is e.g. achieved by a restriction element (not shown) which is arranged for coupling part of the driver force into the housing such restricting the compression force CF with an opposing braking force BF, wherein the positioning force (PF) is the difference between CF and BF. For the following step of compressing the braking force is eliminated, i.e. the restricting element is de-activated.

The named restricting element for driver force restriction may be designed for also taking over the function of the lock 10 and is therefore applicable in particular for systems including a driver spring 3. The restricting element 30 may be activated and/or operated by a person handling the system or it may operate in an at least partially automated manner.

FIGS. 4 to 7 illustrate an exemplary embodiment of a restricting element 30 applicable in the system according to FIG. 3, the restricting element including a cam 31 and a follower 32, wherein the follower 32 (or the cam 31) is fixed to the transmitting piece 1 (or the energy source 1.1) and the cam 31 (or the follower 32) is supported by the housing 2 and rotatable around the housing axis. During the step of positioning and pre-pressing, the cam 31 and the follower 32 are moved relative to each other such that, in the preparatory step, the transmitting piece 1, driven by the driver spring 3, is moved axially under the braking effect of the cam 31 which being supported by the housing counteracts the driver force.

Figure 4:
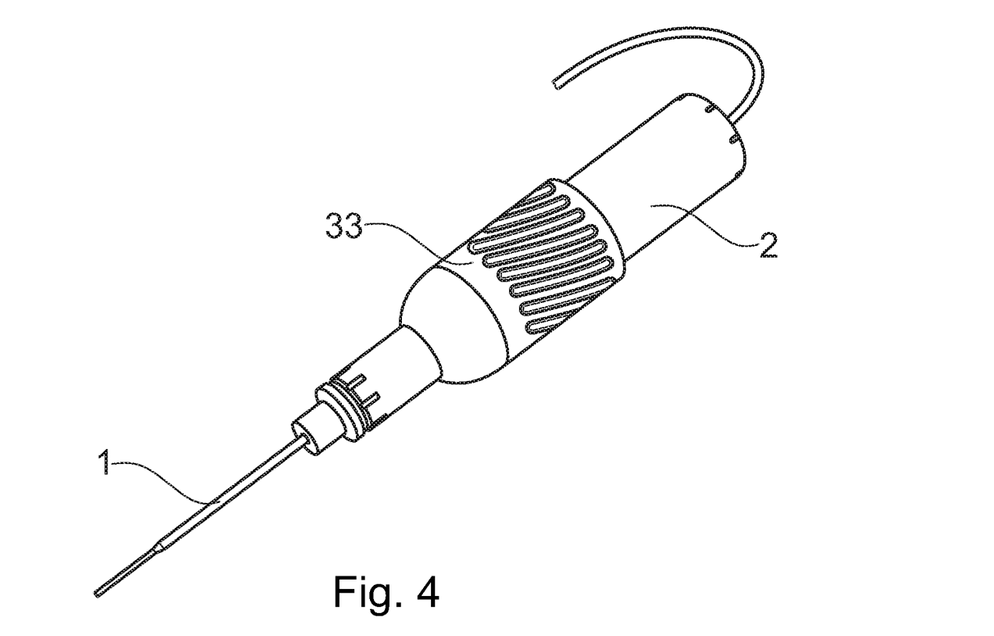
FIGS. 4 to 7 show in further detail an exemplary system according to the invention and parts thereof, the system including a cam and a follower arranged for initially restricting the compression force.
Figure 5:
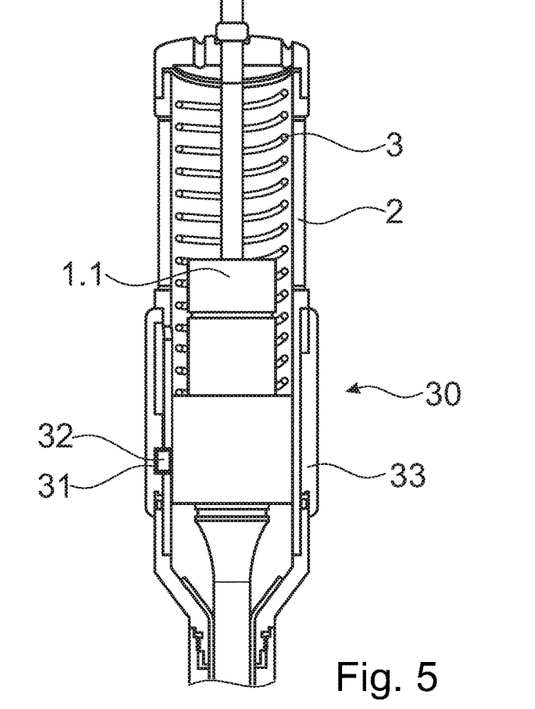

FIGS. 4 and 5 show an ultrasonic hand piece constituting an apparatus applicable in a system as illustrated in FIG. 3, wherein FIG. 4 is a three-dimensional view of the hand piece and FIG. 5 is a view into the partly sectioned hand piece. The follower 32 is arranged fixedly on the energy source and protrudes through e.g. an axially extending groove in the housing into the ring 33 in which the spirally cam 31 is arranged for guiding the follower 32 on its distal side. The ring is rotatable around the housing axis relative to the housing and is supported and guided by the latter. In the step of positioning and pre-pressing (system preparation), the ring 33 is rotated e.g. by the operator handling the apparatus such that the follower 32 together with the transmitting piece 1 (and possibly the energy source) driven by the driver spring 3 and braked by the cam 31 moves in a controlled manner in axial direction. As soon as the distal end of the transmitting piece 1 contacts the proximal face of the pin, further distal movement of the follower is inhibited such that further rotation of the ring 33 distances the cam 31 distally from the follower 32 and the full compression force is coupled into the pin, which means that the preparatory step is completed and the full driver force acts as compression force on the thermoplastic element.

Figure 6:
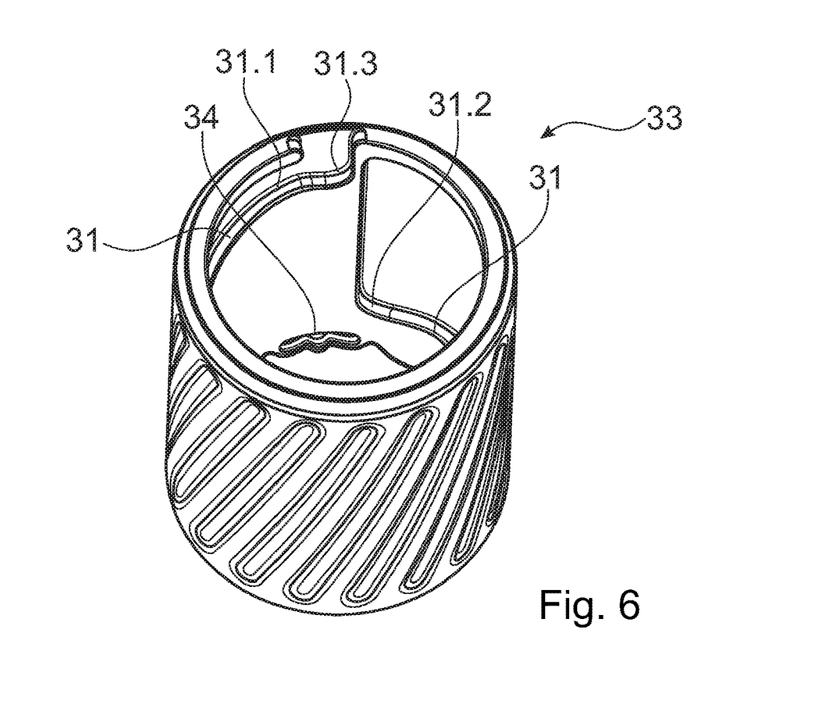

FIG. 6 shows, on a larger scale, the ring 33 with the spirally cam 31 (open cam start 31.1, closed cam end 31.2) arranged on its inside surface, wherein the cam 31 spans in one turn e.g. most of the axial length of the ring. The cam 31 according to FIG. 6 is designed to also function as a lock for locking the transmitting piece in its initial position and the driver spring in a preloaded configuration. For this function, the cam 31 includes beyond its start 31.1 a locking region 31.3 which extends substantially in a radial plane of the ring 33 or preferably constitutes a shallow dish arranged parallel to such a plane. When the follower 32 is situated in the locking region 31.3, the lock is in its locking position. For releasing the lock, i.e. for activation of the driver spring the ring 33 is rotated while moving the follower out of the dish 31.3 necessitating an additional activation force counteracting the driver force.

Preferably, the ring 33 and/or the housing include also a further lock for locking the ring 33 relative to the housing in its rotational end-position, i.e. when the follower is positioned against the closed end 31.2 of the cam. The ring 33 as illustrated in FIG. 6 includes for this function, e.g., an elastically deformable protrusion 34, which cooperates with a corresponding protrusion/depression in the wall of the housing (not shown). For locking the ring 33 relative to the housing, the ring is rotated and therewith the elastically deformable protrusion of the ring is passed with elastic deformation over the protrusion of the housing and enters, relaxing, the depression of the housing, such not only locking the ring 33 relative to the housing but also giving a tactile signal for the operator indicating the end of the preparatory step and that the full compression force is acting on the transmitting piece, i.e. the system is ready for the anchoring process.

Alternative arrangements for locking the ring in its rotational end-position are, e.g., a spring-loaded ball arranged on the housing and cooperating with a protrusion/depression arranged on the ring, wherein during the last part of the ring rotation the spring-loaded ball is forced into its opening by the ring protrusion and relaxes into the opening on further ring rotation such locking the ring relative to the housing.

Figure 7:
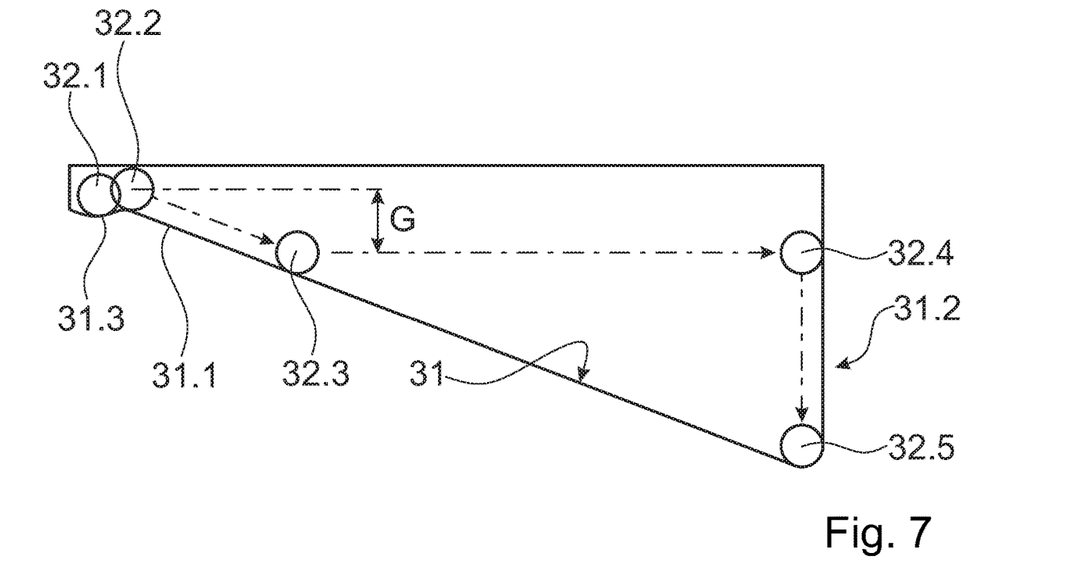

FIG. 7 is a developed view of the cam 31 of the ring 33 illustrated in FIG. 6 and illustrates the movement of the follower 32 guided by the cam 31. The cam 31 shows a cam start 31.1 and a cam end 31.2 and has a constant sloping angle therebetween. Beyond the cam start 31.1 the dished lock portion 31.3 is arranged. FIG. 7 shows the follower in the following five positions: locked initial position 32.1; unlocked initial position 32.2; position 32.3 when a gap of width G is closed, i.e. the transmitting piece is positioned against the thermoplastic element; ready position 32.4 when the ring is fully rotated, i.e. the full driver force acts on the transmitting piece and the thermoplastic element, and the ring is locked to the housing; end position 32.5 in which the follower may arrive through shortening of the thermoplastic element by material liquefaction and displacement (liquefaction step), wherein this shortening may or may not be limited by the end region of the cam.

The cam/follower system as illustrated in FIGS. 6 and 7 is operated in the following manner: (i) pre-loading the driver spring and locking the transmission piece in its initial position by rotating the ring anti-clock-wise for moving the follower from, e.g., position 32.5 into the locked position 32.1; (ii) activating the driver spring by rotating the ring clock-wise for moving the follower out of the lock dish into position 32.2; positioning and pre-pressing the transmitting piece against the thermoplastic element while closing a possible gap by further rotating the ring clock-wise into position 32.3; (iii) de-activating the braking effect of the cam by further rotating the ring clock-wise for moving the follower into position 32.4 and locking the ring relative to the housing. Of the named steps, step (i) belongs to the system assemblage and steps (ii) to (iii) belong to the system preparation. Operation of the cam/follower system of FIGS. 6 and 7 is further illustrated by the flow diagram of FIG. 14.

Depending on the arrangement of the cam 31 in the ring 33, the ring rotation as described above may have an opposite direction, i.e. clock-wise rotation for bringing the follower 32 into position 32.1 and anti-clock-wise rotation for bringing the follower 32 from position 32.1 to position 32.4.

In addition to the tactile signals received by the operator when rotating the ring 33 (increased rotation resistance for locking the follower in its initial position and for locking the ring relative to the housing) or as alternative thereto, it is advantageous to provide visual signals for marking e.g. the same follower positions and ring configurations by e.g. providing the ring 33 with a window and a housing portion, relative to which the ring 33 is rotated, with a stop mark and a start mark, such that, when the follower is in position 32.1, the stop-mark shows through the window, and when the follower is in position 32.4 and the ring is locked, the start-mark shows in the window. Therein the start-mark indicates that the preparatory step of positioning and pre-pressing is carried out, i.e. the gap is closed, and the full compression force acts on the thermoplastic element and therefore the liquefaction process can be started. Instead of the window cooperating with the two marks, it is of course possible to install alternative visual marks or acoustic control means for indicating when the system is ready for the liquefaction process. Electric control means may also be designed for automatically activating the energy source, when the system is ready.

Figure 8:
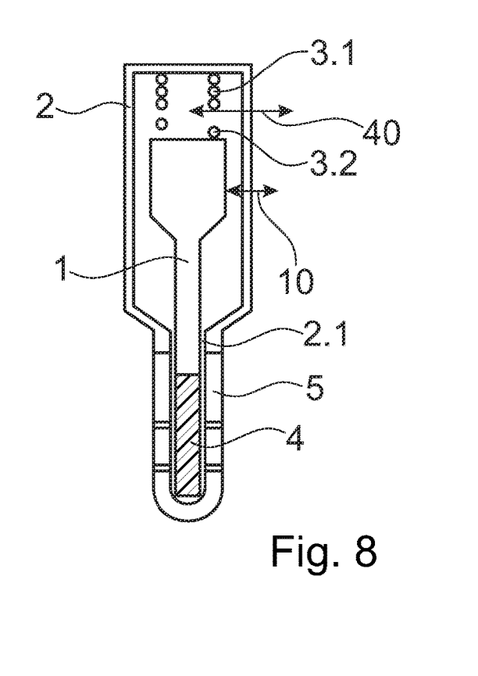
FIG. 8 illustrates, in a very schematic manner, a further exemplary embodiment of the system and method according to the invention, in which the compression force is initially restricted.

FIG. 8 illustrates very schematically a further embodiment of a restricting element, designed for initially restricting the driver force in a system based on the state of the art system as illustrated in FIGS. 1*a* and 1*b*. This restricting element is constituted by an auxiliary lock 40 capable of keeping a main part of the driver spring 3 in a pre-loaded configuration while another part of the driver spring 3 is activated by releasing the lock 10. The same as the lock 10, the auxiliary lock 40 is illustrated by a simple double arrow (left position=locking position, right position=releasing position). In the assembled and pre-loaded system both the lock 10 and the auxiliary lock 40 are in their locking position. For the step of positioning and pre-pressing the transmitting piece 1 against the pin 4, the lock 10 is moved into its releasing position and for the step of compressing, the auxiliary lock 40 is also moved into its releasing position.

Figure 9:
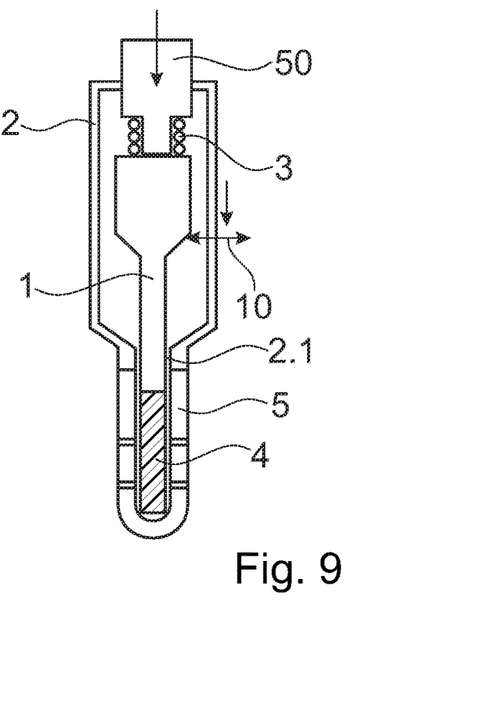
FIG. 9 illustrates, in a very schematic manner, a further embodiment of system and method according to the invention, in which the initial position of the transmitting piece is adapted with the aid of an auxiliary driver.

FIG. 9 shows the principle of a further exemplary embodiment of the system and method according to the invention, wherein the system is based on the state of the art system according to FIGS. 1*a* and 1*b*, but, suitably adapted, is also applicable to be based on the state of the art system according to FIGS. 2*a* and 2*b*, and wherein in the step of positioning and pre-pressing the transmitting piece 1 against the pin 4 is achieved by activation of an auxiliary drive 50 which acts on the transmitting piece 1 while the driver spring may remain locked in the pre-loaded configuration to be released. If the driver spring 3 remains locked during the step of positioning and pre-pressing, this means that the initial position of the transmitting piece 1 and the lock 10 relative to the distal opening 2.1 of the housing 2 is adapted for compensating a possible gap as mentioned above. If the driver spring 3 is released for the step of positioning and pre-pressing, the auxiliary drive is to function as a brake, i.e. as restriction element as discussed in connection with FIG. 9. The auxiliary drive 50 is e.g. operated by an operator of the system or is at least partly automated. The step of positioning and pre-pressing is initiated by activating the auxiliary drive 50 with or without simultaneous releasing of the driver spring 3 and the subsequent step of compressing is initiated by de-activating the auxiliary drive 50 possibly with subsequent release of the driver spring 3.

Figure 10:
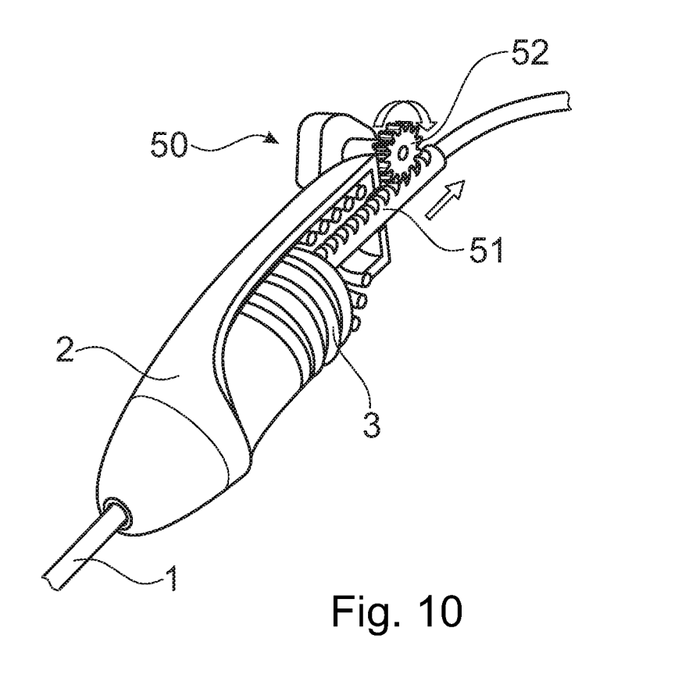
FIGS. 10 and 11 show two exemplary embodiments of the system according to the principle as illustrated in FIG. 9.
Figure 11:
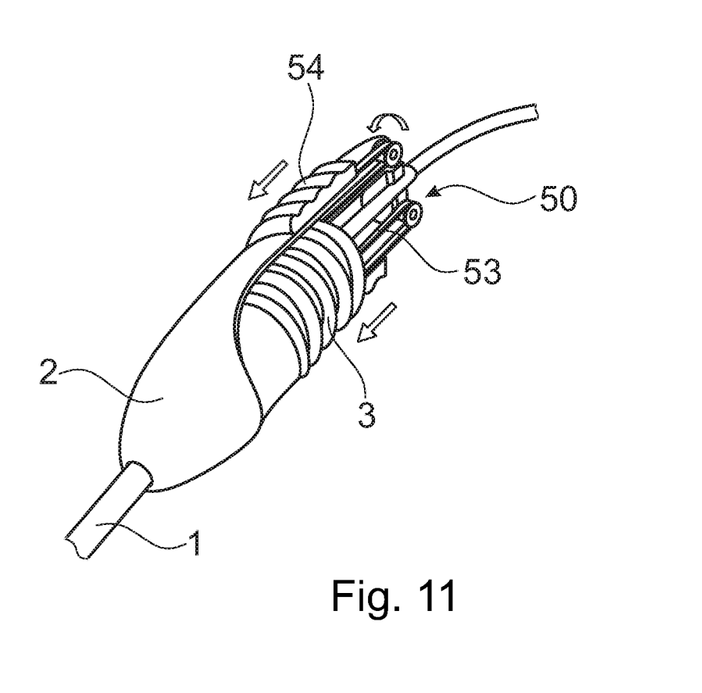

FIGS. 10 and 11 illustrate exemplary embodiments of auxiliary drives 50. According to FIG. 10, the auxiliary drive 50 is a lockable rack and pinion drive (rack 51, pinion 52), which is, e.g., operated by a person handling the apparatus. The rack 51 is coupled to the transmitting piece 1 (possibly via the energy source) and possibly also to the lock 10 (not shown) inside the housing and may protrude from the proximal end of the housing 2 to cooperate with an external pinion 52. The auxiliary drive 50 according to FIG. 11 is a cable drive, wherein cables 53 are operatively connected to the transmitting piece 1 (possibly via the energy source) and possibly to the lock 10 (not shown) inside the housing, and to a drive ring 54 outside of the housing, wherein the drive ring's position relative to the housing 2 and therewith the initial position of the transmitting piece 1 and possibly the lock 10 is adaptable by e.g. cooperating threads on housing 2 and drive ring 54 and by rotation of the drive ring 54 relative to the housing 2.

Figure 12:
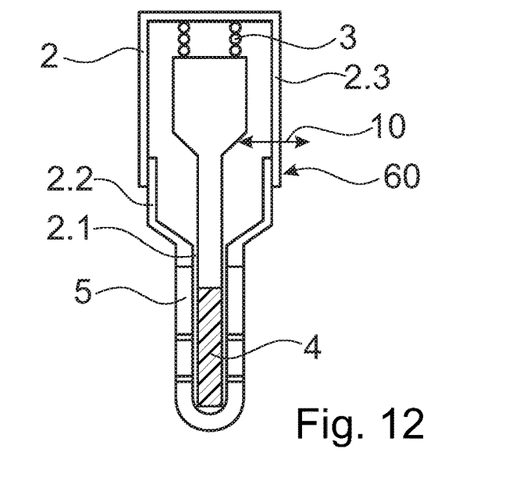
FIG. 12 illustrates, in a very schematic manner, a further embodiment of system and method according to the invention, in which the axial length of the housing is initially adapted.

FIG. 12 illustrates very schematically the principle of a further exemplary embodiment of the system according to the invention, in which system the initial position of the transmitting piece 1 and the lock 10 relative to the distal opening 2.1 of the housing is adapted by adaptation of the axial length of a distal part of the housing 2. Such adaptation is e.g. achieved by a thread connection 60 between a distal housing part 2.2 and a proximal housing part 2.3 and by rotation of the two housing parts 2.2 and 2.3 relative to each other while the transmitting piece 1 and the driver spring remain locked in the proximal housing part 2.3.

Figure 14:
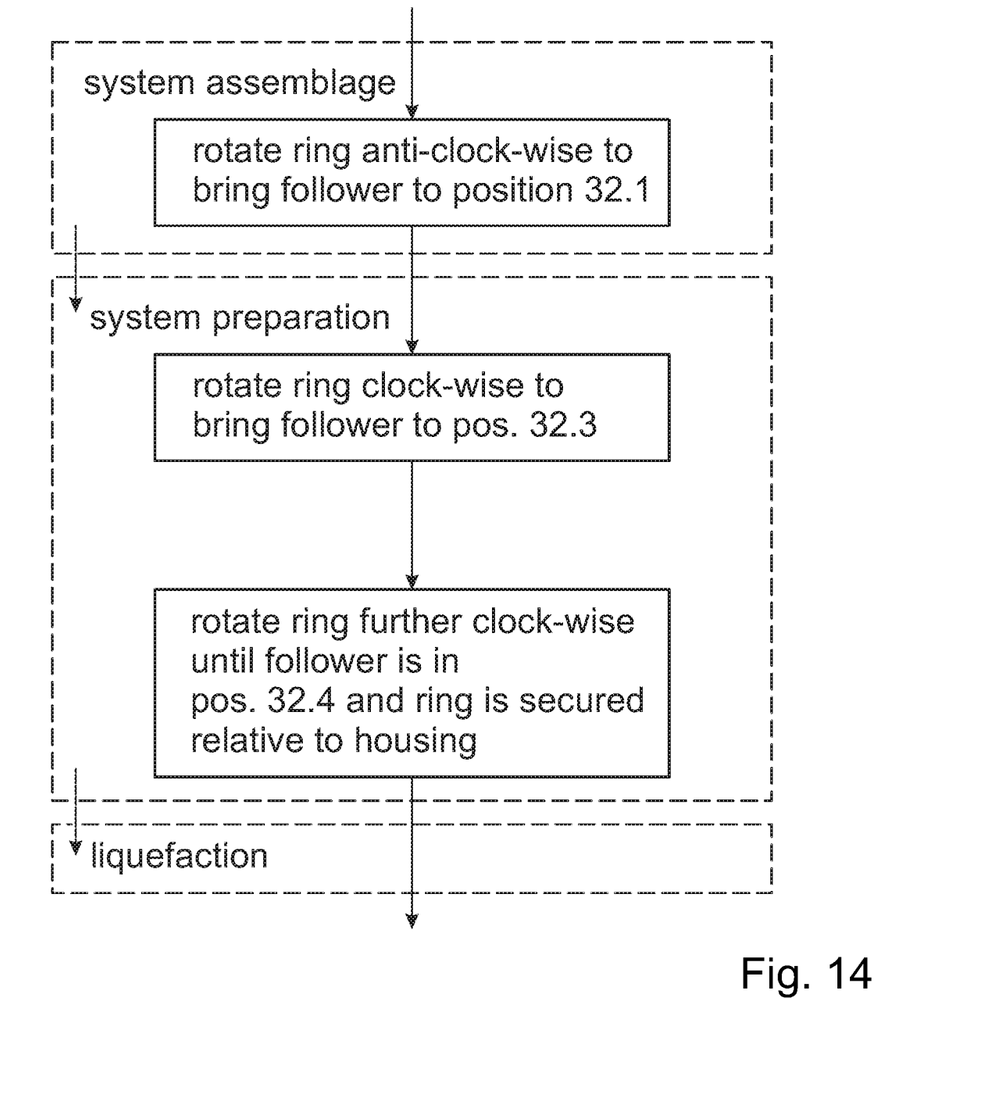
FIG. 14 is a flow-diagram illustrating the handling of the system according to FIGS. 5-7.

FIGS. 13 and 14 are, as mentioned already further above, flow-diagrams, wherein FIG. 13 illustrates a general embodiment of the method according to the invention and FIG. 14 illustrates operation of the cam/follower system as illustrated in FIGS. 6 and 7.

What is claimed is:

1. A system for establishing an anchorage in hard tissue or hard tissue replacement material or for augmenting hard tissue in an operation site of a human or animal patient with the aid of a material having thermoplastic properties and vibration energy, of in situ liquefaction of the material having thermoplastic properties, and of displacement of the material having thermoplastic properties in a liquefied state, the system comprising:
- a transmitting piece connected or connectable to an energy source for generating vibration energy,
- a housing comprising a distal and a proximal end and a longitudinal axis extending therebetween and an opening at the distal end, wherein the transmitting piece is arranged within the housing being movable in the direction of the longitudinal axis, and wherein the opening is adapted to the transmitting piece for a distal portion of the transmitting piece to be able to protrude from the opening,
- a driver suitable for driving the transmitting piece against one of the proximal and the distal ends of the housing, the driver being activatable for exerting a compression force on the transmitting piece,
- a thermoplastic element arranged to be compressible between the transmitting piece and a counter element by the compression force,
- wherein the system is further equipped for shock-free initial positioning and pre-pressing of the transmitting piece against the thermoplastic element,
- wherein the system is equipped for shock-free initial positioning and pre-pressing by comprising a braking element configured to restrict a driver force exerted by the driver to the thermoplastic element, or by comprising an auxiliary drive configured to apply a driver force of the auxiliary drive to the transmitting piece.

2. The system according to claim 1, wherein the equipment for shock-free initial positioning and pre-pressing is constituted by the auxiliary drive, which is designed for restricting the compression force to a smaller positioning force or for exerting the positioning force while the driver is kept in an inactive configuration.

3. The system according to claim 1, wherein the driver is a driver spring being arranged to act between the housing and the transmitting piece and being lockable in a pre-loaded configuration.

4. The system according to claim 1, wherein:
the thermoplastic element is a pin and the counter element is a fenestrated sleeve, and the pin and the sleeve are adapted to each other for the pin to be introducible into the sleeve from a proximal side thereof, or
the thermoplastic element is a tube and the counter element is a collar, and the tube and the collar are adapted to the transmitting piece for a distal portion of the transmitting piece to be able to reach trough the collar and the tube.

5. The system according to claim 3, wherein:
the equipment for shock-free initial positioning and pre-pressing is constituted by the braking element comprising a cam and a follower, and
one of the cam and the follower is arranged on the transmitting piece and the other one is arranged to be moveable relative to the transmitting piece and the housing for allowing controlled axial movement of the transmitting piece relative to the housing.

6. The system according to claim 5, wherein the follower is fixedly arranged relative to the transmitting piece and wherein the cam is arranged on the inside of a ring arranged to be rotatably supported by the housing.

7. The system according to claim 6, wherein the cam further comprises a locking part for locking the follower and therewith the transmitting piece in an initial position.

8. The system according to claim 7, wherein the locking part is dish-shaped.

9. The system according to claim 6, wherein at least one of the housing and the ring are equipped for locking the ring relative to the housing when the follower has reached an end of the cam.

10. The system according to claim 3, wherein the equipment for shock-free initial positioning and pre-pressing further comprises an auxiliary lock for keeping a part of the driver spring preloaded.

11. The system according to claim 2, wherein the auxiliary drive is a rack and pinion drive or a cable drive.

12. The system according to claim 11, wherein the auxiliary drive operates at least partly outside of the housing.

13. The system according to claim 1, wherein the driver is an electric drive.

14. An apparatus suitable for the system according to claim 1, the apparatus comprising the transmitting piece, the housing, the driver, and the braking element or the auxiliary drive.

15. The apparatus according to claim 14, wherein the auxiliary drive is designed for restricting the compression force to a smaller positioning force or for exerting the positioning force while the driver is kept in an inactive configuration.

* * * * *